United States Patent
Harouaka et al.

(10) Patent No.: US 11,885,793 B1
(45) Date of Patent: Jan. 30, 2024

(54) REAL-TIME PATCH-CLAMP SENSING OF TRANSPORT ACROSS A BARRIER TISSUE

(71) Applicant: National Technology & Engineering Solutions of Sandia, LLC, Albuquerque, NM (US)

(72) Inventors: Ramdane Abdallah Harouaka, Livermore, CA (US); Michael Bartsch, Foster City, CA (US); Jennifer Lauren Schwedler, Livermore, CA (US); Brooke Nicole Harmon, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 427 days.

(21) Appl. No.: 17/074,221

(22) Filed: Oct. 19, 2020

(51) Int. Cl.
| | | |
|---|---|---|
| *G01N 33/487* | (2006.01) | |
| *B01L 3/00* | (2006.01) | |
| *C12M 1/34* | (2006.01) | |
| *C12M 3/00* | (2006.01) | |
| *C12M 1/12* | (2006.01) | |

(52) U.S. Cl.
CPC .... *G01N 33/48728* (2013.01); *B01L 3/50273* (2013.01); *C12M 1/3407* (2013.01); *C12M 3/00* (2013.01); *C12M 25/04* (2013.01); *C12M 25/14* (2013.01)

(58) Field of Classification Search
CPC ................................................ G01N 33/48728
See application file for complete search history.

(56) References Cited

U.S. PATENT DOCUMENTS

2006/0166185 A1* 7/2006 Vodanoy .......... G01N 33/48728
205/777

OTHER PUBLICATIONS

Gillis, "Admittance-based measurement of membrane capacitance using the EPC-9 patch-clamp amplifier", 1999, Eur J Physiol, 439, pp. 655-664. (Year: 1999).*
Bak, M. et al., "Penetrating the blood brain barrier—DTU Nanotech" (Jan. 2018), downloaded from the internet Sep. 18, 2020 from https://www.n.anotech.dtu.dk/samples-newsletter/jan-18/blood-brain.
Ball, K., et al., "Physiologically based pharmacokinetic modelling of drug penetration across the blood-brain barrier-towards a mechanistic IVIVE-based approach," *The AAPS Journal*, (Oct. 2013); 15(4): 913-932.
Brazil, R., "A barrier to progress: getting drugs to the brain", The Pharmaceutical Journal, (May 15, 2017), vol. 298, No. 7901, online | DOI: 10.1211/PJ.2017.20202723, downloaded from the Internet Sep. 18, 2020 from https://www.irbbarcelona.org/en/news/a-barrier-to-progress-getting-drugs-to-the-brain.
Bruhn, B.R., et al., "Dual-pore glass chips for cell-attached single-channel recordings," *Lab on a Chip*, (Jul. 21, 2014); 14(14): 2410-2417.

(Continued)

*Primary Examiner* — Jonathan M Hurst
(74) *Attorney, Agent, or Firm* — Samantha Updegraff; Fish & Richardson (57) ABSTRACT

The present disclosure relates to methods, apparatuses, and systems to measure one or more electrical signals from a cultured cell layer. In some embodiments, such electrical signals can be indicative of transport or lack of transport of an agent through the cell layer.

7 Claims, 8 Drawing Sheets

(56) References Cited

OTHER PUBLICATIONS

Chang, T.Y., et al., "Cell and protein compatibility of parylene-C surfaces," Langmuir, (Aug. 9, 2007); 23(23): 11718-11725.
Chen, P. et al., "Development of planar patch clamp technology and its application in the analysis of cellular electrophysiology", Progress in Natural Science, (Feb. 10, 2009),19(2):153-60.
Chodobski, A., B.J. Zink, and Szmydynger-Chodobska J., "Blood-brain barrier pathophysiology in traumatic brain injury," Translational Stroke Research, (Dec. 2011); 2(4): 492-516.
Daneman, R. and A. Prat, "The blood-brain barrier", *Cold Spring Harbor Perspectives in Biology*, (Jan. 2015); 7(1): a020412 (23 pp.).
Debus, K. and M. Lindau, "Resolution of patch capacitance recordings and of fusion pore conductances in small vesicles," *Biophysical Journal*, (Jun. 2000); 78(6): 2983-2997.
Fertig, N., et al., "Stable integration of isolated cell membrane patches in a nanomachined aperture," *Applied Physics Letters*, (Aug. 21, 2000); 77(8): 1218-1220.
Fertig N., et al., "Microstructured glass chip for ion-channel electrophysiology," *Physical Review E*, (Sep. 21, 2001), 64(4): 040901 (4 pp.).
Lindau, M. and E. Neher, "Patch-clamp techniques for time-resolved capacitance measurements in single cells," *Pflügers Archiv European Journal of Physiology*, (Feb. 1988); 411(2): 137-146.
Martinez, D., et al., "High-fidelity patch-clamp recordings from neurons cultured on a polymer microchip." Biomed Microdevices, (Dec. 2010), 12(6):977-85. doi: 10.1007/s10544-010-9452-z. PMID: 20694518.
Neher, E. and B. Sakmann, "The patch clamp technique," *Scientific American*, (Jan. 9, 1992); 266(3): 44-51.
O'Brown, N.M., S.J. Pfau, and C. Gu, "Bridging barriers: a comparative look at the blood-brain barrier across organisms", *Genes & Development*, (Apr. 1, 2018); 32(7-8): 466-478.
Paddock, C., "Alzheimer's disease: Could a leaky blood-brain barrier be involved?", (May 31, 2016), Medical News Today, 5 pages. Downloaded from the internet Sep. 18, 2020 from https://www.medicalnewstoday.com/articles/310639.
Pantoja, R., et al., "Silicon chip-based patch-clamp electrodes integrated with PDMS microfluidics," *Biosensors and Bioelectronics*, (May 6, 2004), 20(3): 509-517.
Pusch, M. et al., "Rates of diffusional exchange between small cells and a measuring pipette", (Mar. 1988), Pflügers Archiv—European Journal of Physiology 411(2):204-11, DOI: 10.1007/BF00582316.
Py, C, et al., "A novel silicon patch-clamp chip permits high-fidelity recording of ion channel activity from functionally defined neurons", Biotechnol Bioeng., (Nov. 1, 2010);107(4):593-600. doi: 10.1002/bit.22834. PMID: 20648547.
Rituper, B., et al., "High-resolution membrane capacitance measurements for the study of exocytosis and endocytosis," *Nature Protocols*, (May 23, 2013), 8(6): 1169-1183.
Sakaba T., Hazama A., Maruyama Y., "Patch-Clamp Capacitance Measurements", in Okada Y. (eds) *Patch Clamp Techniques*, (Apr. 27, 2012), Springer Protocols Handbooks. Springer (Tokyo, Japan), pp. 277-286. https://doi.org/10.1007/978-4-431-53993-3_17.
Sordel, T., et al., "The development of high quality seals for silicon patch-clamp chips," *Biomaterials*, (Oct. 2010); 31(28): 7398-7410.
Thompson, R. E, Lindau, M., Webb, W. W., Robust, high-resolution, whole cell patch-clamp capacitance measurements using square wave stimulation. Biophysical journal. (Aug. 1, 2001);81(2):937-48.
"Traumatic Brain Injury" downloaded from the internet Sep. 18, 2020 from https://dod.defense.gov/News/Special-Reports/0315_tbi/, 5 pages.
Wiley, D.T., et al., "Transcytosis and brain uptake of transferrin-containing nanoparticles by tuning avidity to transferrin receptor," *Proceedings of the National Academy of Sciences of the United States of America*, (May 21, 2013), 110(21): 8662-8667.
Zhang, L., et al., "Enhanced parylene-C fluorescence as a visual marker for neuronal electrophysiology applications," *Lab on a Chip*, (Dec. 7, 2018); 18(23): 3539-3549.

* cited by examiner

REAL-TIME PATCH-CLAMP SENSING OF TRANSPORT ACROSS A BARRIER TISSUE

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD

The present disclosure relates to methods, apparatuses, and systems to measure one or more electrical signals from a cultured cell layer. In some embodiments, such electrical signals can be indicative of transport or lack of transport of an agent through the cell layer.

BACKGROUND

There has been considerable investment towards the development of model systems that can be used to screen agents and compounds for efficiency of delivery into the central nervous system. Commonly used assays based on optical imaging, sensing of radiological labels, and mass spectrometry generally rely on snapshots collected at time points before and after exposure to a compound of interest.

SUMMARY

The present disclosure relates to real-time, electrical sensing of transport across barrier tissues. In particular embodiments, electrical sensing can include highly sensitive detection of changes in capacitance that occur when a lipid vesicle fuses with a patched membrane surface. Thus, in one embodiment, the present disclosure includes methods of detecting active transport in functional barrier tissues in real-time as vesicles are formed on one surface of a cell and then transported across to the opposite side. Such methods can include culturing endothelial cells over pore structures, thereby encouraging the formation of gigaohm sealed patches over the pore.

In a first aspect, the present disclosure encompasses a method including: culturing a plurality of barrier cells on a first surface of a substrate and within a first chamber, wherein the substrate includes at least one pore disposed within the substrate; exposing the first chamber to an agent; and measuring one or more electrical signals within the first chamber or within a second chamber in fluidic communication with the at least one pore.

In some embodiments, the substrate includes one or more pores. In other embodiments, at least one pore is a micropore or a nanopore. In yet other embodiments, a seal is formed between at least one pore and at least one barrier cell.

In some embodiments, the one or more electrical signals is indicative of transport or lack of transport of the agent through the at least one barrier cell. In other embodiments, the one or more electrical signals is indicative of a membrane capacitance or a change in membrane capacitance in the at least one barrier cell.

In some embodiments, the first chamber includes a gas, a buffer, or a biological fluid. In other embodiments, the agent includes a small molecule, a drug, a protein, a peptide, a nucleic acid, or a detection agent. In particular embodiments, the transport is active transport, passive transport, transcytosis, vesicle-mediated transcytosis, receptor-mediated transcytosis, or adsorptive transcytosis.

In some embodiments, the substrate includes a plurality of pores, the second chamber includes a plurality of wells, and each well is configured to be in fluidic communication with one pore.

In some embodiments, the method includes a probe or an array of individually addressable probes, wherein at least one probe is configured to be in fluidic communication with one well and wherein the at least one probe is configured to detect an electrical signal within a fluid disposed within the one well. In further embodiments, said measuring includes: measuring the one or more electrical signals within each of the plurality of wells by using each of the probe or each of the individually addressable probes, thereby providing a plurality of spatially resolved electrical measurements.

In some embodiments, the method further includes (e.g., prior to said culturing): pre-treating the first surface of the substrate with a chemical agent, a biological agent, or a plasma.

In some embodiments, said measuring includes: separating the one or more signals into a capacitive component and a conductance component; and determining a membrane capacitance or a change in membrane capacitance based on the capacitive component and the conductance component.

In a second aspect, the present disclosure includes an apparatus including: a first chamber configured to culture a layer including a plurality of barrier cells; a substrate including one or more pores disposed within the substrate, wherein at least one pore is configured to form a seal with at least one barrier cell, and wherein at least one pore is a micropore or a nanopore; and a second chamber in fluidic communication with the at least one pore.

In some embodiments, a surface of the substrate and/or the at least one pore includes a conformal layer of a polymer. In other embodiments, the substrate includes a plurality of pores, the second chamber includes a plurality of wells, and each well is configured to be in fluidic communication with one pore. In yet other embodiments, the apparatus further includes a probe or an array of individually addressable probes, wherein at least one probe is configured to be in fluidic communication with one well and wherein the at least one probe is configured to detect an electrical signal within a fluid disposed within the one well.

In a third aspect, the present disclosure encompasses a system including: an apparatus (e.g., any described herein); a probe configured to detect an electrical signal within a fluid disposed within the second chamber; and a circuit configured to receive the electrical signal as an input signal and to transmit a real component and an imaginary component of complex admittance as output signals. In some embodiments, the circuit includes: a lock-in amplifier configured to receive an electrical signal from the probe and to transmit an initial real component and an initial imaginary component of complex admittance as output signals; and a device configured to receive the output signals and to transmit a determined membrane capacitance as an output. In some embodiments, the determined membrane capacitance can be a relative capacitance between a patch of membrane (of the at least one barrier cell) forming the sealed with the at least one pore and a capacitance of the rest of the barrier cell(s).

In other embodiments, the circuit further includes: a low-pass filter configured to receive the initial real component and the initial imaginary component and to transmit a filtered real component and a filtered imaginary component; and an analog-to-digital converter (ADC) configured to receive the filtered real component and the filtered imaginary component and to transmit a corresponding digital real component signal and a corresponding imaginary component signal. In further embodiments, the device is configured to receive the corresponding digital real component signal and the corresponding imaginary component signal and to transmit a determined membrane capacitance as an output.

In a fourth aspect, the present disclosure a system including: an apparatus (e.g., any described herein); a probe configured to detect an electrical signal within a fluid disposed within the second chamber; a circuit configured to receive an electrical signal from the probe and to transmit a current measurement; and a device configured to receive the current measurement and to transmit a determined membrane capacitance as an output. In some embodiments, the determined membrane capacitance can be a relative capacitance between a patch of membrane (of the at least one barrier cell) forming the sealed with the at least one pore and a capacitance of the rest of the barrier cell(s).

In some embodiments, the circuit further comprises: a voltage generator or a function generator to generate a voltage step provided to the apparatus, the layer, or the plurality of barrier cells; and/or an amplifier configured to receive the electrical signal from the probe and to transmit an amplified current measurement, wherein the device configured to receive the amplified current measurement and to transmit a determined membrane capacitance as an output.

In any embodiment herein, the plurality of barrier cells includes a layer of cells (e.g., mammalian cells, non-mammalian cells, endothelial cells, epithelial cells, and other associated cells that can typically form selective, semipermeable borders between different biological niches).

In any embodiment herein, the seal is characterized as a gigaohm seal.

In any embodiment herein, a first surface of the substrate, a second surface of the substrate, and/or a surface of the at least one pore includes glass, silicon, silicon dioxide, silicon nitride, a semiconductor material, a conformal layer of a polymer, a photoresist, or a combination thereof.

Additional details follow.

Definitions

As used herein, the term "about" means +/−10% of any recited value. As used herein, this term modifies any recited value, range of values, or endpoints of one or more ranges.

By "chamber" is meant a two-dimensional or three-dimensional region of the fluidic device configured to confine a fluid (e.g., a gas, a liquid, a colloid, a solution, etc.). This region may be enclosed within a substrate and include one or more ports or channels in fluidic communication with that region. Alternatively, the region can have an open format and may not be enclosed. The chamber can have any useful configuration (e.g., a channel, a well, a tube, a pipe, etc.) and dimension (e.g., a chamber, a microchamber, or a nanochamber, including fluidic channels, millifluidic channels, microchannels, nanochannels, microwell, and nanowells) having one or more optional ports.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "micro" is meant having at least one dimension that is less than 1 mm and, optionally, equal to or larger than about 1 µm. For instance, a microstructure (e.g., any structure described herein) or a micropore (e.g., any pore described herein) can have a length, width, height, cross-sectional dimension, circumference, radius (e.g., external or internal radius), or diameter that is less than 1 mm.

By "nano" is meant having at least one dimension that is less than 1 µm but equal to or larger than about 0.1 nm. For instance, a nanostructure (e.g., any structure described herein) or a nanopore (e.g., any pore described herein) can have a length, width, height, cross-sectional dimension, circumference, radius (e.g., external or internal radius), or diameter that is less than 1 µm.

As used herein, the terms "top," "bottom," "upper," "lower," "above," and "below" are used to provide a relative relationship between structures. The use of these terms does not indicate or require that a particular structure must be located at a particular location in the apparatus.

BRIEF DESCRIPTION OF THE DRAWINGS

FIG. 7 shows a graph of seal test results for resistances measured across micropores. Data are provided for a Nanion chip (empty or with cultured cells); a micropore array (empty or with cultured cells); a micropore within an SU8 disc sealed with parylene (empty or with cultured cells); and a bath, which indicates the measured short circuit resistance through 0.1 M phosphate-buffered saline (PBS) buffer.

DETAILED DESCRIPTION

The present disclosure allows for real-time quantification of cross-barrier transport based on label-free detection of electrical signals. For instance, patch-clamp is a highly sensitive micropipette recording technique that is commonly used in electrophysiology to record activity of individual ion channels on cell membranes. It involves forming a tight gigaohm seal against the surface of a membrane and amplifying the electrical response across the membrane patch in response to an applied voltage or current clamp. The method has also been used to quantify vesicle fusion to membranes through measurement of capacitance, with a resolution sufficient for detecting individual vesicles. While capacitance-based detection of exocytosis and endocytosis has been demonstrated for various cells, to our knowledge, patch-clamp has not been previously applied to investigate transport across an adherent endothelial barrier tissue that remains functionally active.

Accordingly, described herein are methods, apparatuses, and systems that involve culturing endothelial cells over pore structures and encouraging the formation of gigaohm sealed patches. Once the seal is successfully formed, amplification and phase-tracking strategies can be used to measure capacitance in the cell-attached configuration of patch-clamp. Also described herein are arrays of pores, which can be used with individually addressable electrodes to allow the setup of experiments with increased levels of spatiotemporal resolution. This strategy could also allow for recording to continue from a percentage of pores in the event that gigaohm seals are transient and can be formed and released repeatedly by living endothelial cells.

A barrier cell can be any biological cell that forms a barrier on the pore separating the first and second chambers. Non-limiting barrier cells include those within a biofilm, a monolayer film, a multilayer film, a layer of cells, or other cellular assembly. Yet other non-limiting barrier cells can include non-mammalian cells (e.g., such as bacteria that form a biofilm, mammalian cells, endothelial cells, epithelial cells, and other associated cells that can typically form selective, semipermeable borders between different biological niches).

Figure 1:
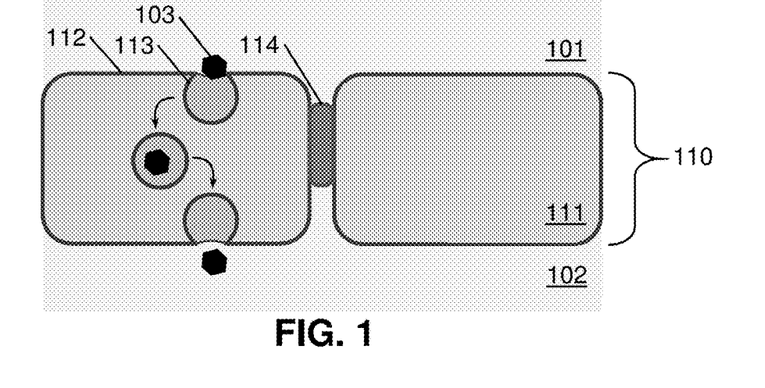
FIG. 1 shows a non-limiting schematic of transport of an agent 103 through a barrier cell 111.

In one instance, such barrier cells form a blood-brain barrier (BBB), in part, of endothelial cells (e.g., brain microvascular endothelial cells (BMECs)), which form a barrier between circulating blood and tissues of the central nervous system (CNS). FIG. 1 provides a simplified, non-limiting schematic, in which a layer 110 of barrier cells 111 form a barrier between the blood component 101 and the brain component 102. Typically, this layer 110 restricts access to the brain, and any access is highly regulated. Cell-to-cell junctions 114 can include a tight junction or an adherens junction that is formed by various membrane proteins (e.g., claudin, occludin, zona occludin, cadherin, catenin, vinculin, etc.). These junctions serve to minimize paracellular transport of agents into the brain.

In certain instances, an agent 103 can be actively transported through the barrier cell 111. Various transport mechanisms exist, including by way of diffusion or transcellular lipophilic pathways, paracellular aqueous pathways through tight junction, vesicle-mediated transcytosis, receptor-mediated transcytosis, transport protein-based pathways, or adsorptive transcytosis. In one embodiment, transcytosis can include association of the agent 103 to the luminal side (in proximity to blood 101) of the membrane 112 for the barrier cell 111, formation of a vesicle 113, migration of the vesicle through the cell, attachment of the vesicle to the abluminal or basal side (in proximity to the brain 102) of the barrier cell 111, and then release of the agent 103 into the brain 102. As can be seen, prior to release of the agent 103, the vesicle 113 attaches to the abluminal side of the cell membrane, in which this attachment results in a transient increase in the surface area of that membrane. Thus, if transcytosis is associated with endocytosis and exocytosis events, then vesicle attachment to the cell membrane will be associated with changes in surface area to the cell membrane.

By using electrophysiology measurements, such changes in surface area can be detected in a label-free manner. For instance, a cell can be modeled as a minimal equivalent circuit, in which the cell membrane is represented by a parallel capacitor and a resistor that are connected in series. The capacitor is characterized by a membrane capacitance ($C_m$), and the resistor is characterized by a membrane conductance ($G_m$). As used herein, $C_m$ can refer to an absolute value or a relative value. In particular embodiments herein, $C_m$ is a relative capacitance between the patch of membrane sealed in the pore and the capacitance of the rest of the barrier (including the rest of the cell membrane with likely contributions from other attached cells). Unlike configurations for a single layer patch clamp (e.g., whole cell configuration) that provides an absolute capacitance measurement, a relative $C_m$ measurement can be more sensitive to small changes in capacitance and less susceptible to capacitance noise.

$C_m$ can be measured by applying a voltage across the circuit (or cell), measuring the resulting current, and then deconvolving the components of the current to arrive at $C_m$. In one instance, voltage can be applied as a step, and the measured current is then fit to an exponential decay function to provide estimates of amplitude, time constant, and baseline parameters. These parameters, in turn, can be used to provide $C_m$. In another instance, voltage is applied as a sinusoidal signal, and the resultant current is separated into real (Re) and imaginary (Im) components by a lock-in amplifier. By choosing an appropriate phase setting, the outputs of the lock-in amplifier will provide the Re and Im components (conductance and capacitive components, respectively) for the complex admittance of the network, which can then be used with the D.C. conductance value to provide $C_m$. Further methods and processes to determine $C_m$ are provided, e.g., in Rituper, B., et al., "High-resolution membrane capacitance measurements for the study of exocytosis and endocytosis," *Nature Protocols*, 2013; 8(6):

1169-1183); Lindau, M. and E. J. P. A. Neher, "Patch-clamp techniques for time-resolved capacitance measurements in single cells," *Pflügers Archiv European Journal of Physiology*, 1988; 411(2): 137-146; Debus, K. and M. Lindau, "Resolution of patch capacitance recordings and of fusion pore conductances in small vesicles," *Biophysical Journal*, 2000; 78(6): 2983-2997; and Pusch, M. and E. Neher, "Rates of diffusional exchange between small cells and a measuring patch pipette," *Pflügers Archiv European Journal of Physiology*, 1988; 411(2): 204-211, each of which is incorporated herein by references in its entirety.

Electrophysiology measurements can be provided by using any apparatus or system configured to measure electrical signals in proximity to a cell. In particular embodiments, the signal is measured on a patch of a cellular membrane that forms an electrical contact (or a seal) with a pore. In order to minimize access resistance and capacitance noise, the seal can be a gigaohm seal (e.g., having a seal resistance of 109 ohm or greater), in certain non-limiting instances.

The first and second chambers can be disposed in any useful manner. In some embodiments, the apparatus or the system includes a substrate having a pore, a first chamber disposed in proximity to a first surface of the substrate or in fluidic communication with a first surface of the substrate, and a second chamber disposed in proximity to a second surface of the substrate or in fluidic communication with a second surface of the substrate. In one embodiment, the substrate is planar having a top surface and a bottom surface, in which case the first surface is one of the top or bottom surfaces and the second surface is the other surface. A pore (or aperture) extends from the first surface to the second surface of the substrate. In this way, the pore (without a barrier cell) provides fluidic communication between the first and second chambers. One of the chambers can be configured to receive the barrier cell, and the other chamber can be configured to be electrically connected to a circuit to provide an electrical measurement. In some non-limiting embodiments, the first chamber is an upper chamber, and the second chamber is a lower chamber.

In particular embodiments, the apparatus or the system includes a substrate having a micropore, an upper chamber disposed above the substrate or in fluidic communication with a top surface of the substrate, and a lower chamber disposed below the substrate or in fluidic communication with a bottom surface of the substrate. The micropore, in turn, is an aperture within a substrate, in which the aperture extends from the top surface to the bottom surface of the substrate.

In this way, the micropore (without a barrier cell) provides fluidic communication between the upper and lower chambers. The upper chamber is generally configured to store the barrier cell, and the lower chamber is generally configured to be electrically connected to a circuit to provide an electrical measurement.

The pore can have any useful shape (e.g., a circle, an oval, a square, etc.). The pore can be characterized, e.g., by a pore having a dimension (e.g., a diameter or other dimension of the aperture that is parallel to the top or bottom surface of the substrate) of from about 1 nm to about 250 µm (e.g., from 1 nm to 1 µm, 1 nm to 5 µm, 1 nm to 10 µm, 1 nm to 50 µm, 1 nm to 100 µm, 1 nm to 200 µm, 1 µm to 5 µm, 1 µm to 10 µm, 1 µm to 20 µm, 1 µm to 50 µm, 1 µm to 100 µm, or 1 µm to 200 µm). In other embodiments, the pore can be a micropore or a nanopore.

A length of the pore extending through the substrate (e.g., and orthogonal to the top or bottom surface of the substrate) can be any as determined by a skilled artisan to provide a useful entry resistance, which can be dominated by the smallest dimension of the pore. In some instance, the length of the pore is greater than a diameter of the pore. Such lengths can be from about 1 nm and up to 500 µm, 1 mm, or longer. In some embodiments, the sidewall of the aperture can be characterized by an angle of about 40° to about 140°, including 80° to about 100°. In other embodiments, the sidewall can be linear or curvilinear.

The substrate can have one or more pores disposed within the substrate. A plurality of pores can be arranged in any useful geometry or array, such as a m×n array, in which each of m and n is, independently, an integer from 1 to 100. The substrate can be formed from any useful material, such as an epoxy, a photoresist, a polymer, etc. The substrate and/or the pore(s) can be further coated with a layer of a polymer, e.g., parylene-C, silicone, acrylic, etc.; a biocompatible polymer; a carbohydrate; an adhesion protein; or a protein, e.g., poly-L-lysine, fibronectin, laminin, etc. Such layers for the polymer can optionally be a conformal layer. The first and second chambers can be formed from any useful material, such as a polymer (e.g., a siloxane, such as poly(dimethyl siloxane)).

Other non-limiting materials for the substrate, first chamber, or second chamber can include epoxy, photoresist, poly(carbonate), quartz, glass, silica, fused-silica, silicon, silicon oxide, silicon nitride, silicon oxynitride, silicon carbide, poly(dimethyl siloxane), a polymer, a metal, a semiconductor, or a transparent substrate, as well as composites and multi-layered, laminated, or bonded forms thereof. Exemplary methods of fabrication include rapid prototyping, microfabrication (e.g., by casting, injection molding, compression molding, embossing, ablation, thin-film deposition, and/or Computer Numerically Controlled (CNC) micromachining), photolithography, etching techniques (e.g., wet chemical etching, reactive ion etching, inductively coupled plasma deep silicon etching, laser ablation, or air abrasion techniques), methods for integrating these structures into high-throughput analysis equipment (e.g., integration with a microplate reader or a control instrument, such as a computer), methods for fabricating and integrating valves (e.g., one or more pneumatic valves), methods for integrating structures with a transducer array, methods for modifying surfaces (e.g., by including a layer of extracellular matrix components, such as with a protein solution, poly(lysine), fibronectin (FN), laminin, Matrigel™ and/or RGD peptide, or by including a layer of a globulin protein, such as albumin or an immunoglobulin), and methods for providing vias or inlets (e.g., by piercing, drilling, ablating, or laser cutting), such as those described in U.S. Pat. No. 8,257,964; and U.S. Pub. Nos. 2012/0231976, 2012/0214189, 2011/0129850, 2009/0251155, and 2009/0036324, each of which is incorporated herein by reference in its entirety.

To form a seal, the barrier cell can be cultured on a substrate having the pore(s). At least one pore can be configured to form a seal with at least one barrier cell. Non-limiting barrier cells include brain microvascular endothelial cells (BMECs), such as primary or low passage BMECs; cerebral microvascular endothelial cells, including human cerebral microvascular endothelial cells (hCMECs); cerebral endothelial cells, including human cerebral endothelial cells; human pluripotent stem cells (hPSC) used to generate differentiated endothelial cells, e.g., hPSC-derived endothelial cells; and others. Optionally, the culture can be characterized as a confluent layer having tight junctions and/or adherens junctions.

Sealing can be enhanced by providing sufficient incubation time of the barrier cells on the surface of the substrate. Other techniques to enhance sealing can include using a protein that enhances adhesion between the barrier cells and the substrate, in which the protein can include poly-L-lysine, an extracellular matrix (ECM) protein, etc.; employing a co-culture of different cell types, such as BMEC with other cell types (e.g., astrocytes, pericytes, neurons, stem cells, etc.) in either the same chamber or in different chambers; use of flow over the barrier cells during culture on the substrate; selecting a material for the substrate or the coating on the substrate that promotes cellular adhesion; and/or treating the surface of the substrate to promote cellular adhesion (e.g., plasma treatment).

In use, the methods, systems, and apparatuses herein can provide a BBB model, which can be used to test the ability of an agent to cross the barrier layer. In one embodiment, the method can include exposing the first chamber to an agent and then measuring one or more electrical measurements in the second chamber. For instance, changes in $C_m$ can indicate transcytosis of the agent across the barrier layer. An agent can be any substance capable of being transported across the barrier cell. Non-limiting agents include a small molecule drug, a protein, a peptide, a nucleic acid, a detection agent, an enzyme, an antibody, etc.

The first and second chambers can include any useful fluid, such as a gas, air, a buffer, an electrolyte, an ionic solution, or a biological fluid. In one instance, the first chamber having the barrier cells can include blood, plasma, blood components, blood proteins, red blood cells, etc.

In the second chamber, electrical signals can be measured in any useful manner. In one non-limiting instance, the first chamber is grounded by being electrically connected to a grounded electrode, and the second chamber is in electrical connection with a probe or a circuit to measure electrical signals in proximity to the pore. In some embodiments, the circuit is configured to measure current. In other embodiments, the circuit is configured to receive an electrical signal; separate an electrical signal into a real component and an imaginary component of complex admittance as output signals; and to convert such output signals as values for $C_m$.

The circuit can include any useful components, such as a probe (e.g., an electrode) configured to provide an electrical signal measured in the second chamber, such as a current; a stimulator configured to apply a voltage step or a sinusoidal voltage to the cell; an amplifier (e.g., a lock-in amplifier) configured to receive the electrical signal from the probe and transmit an amplified signal or components (e.g., real and imaginary components) of a complex admittance signal; a filter (e.g., a low-pass filter) configured to receive a signal from the probe and/or the amplifier and to transmit a filter signal; an analog-to-digital converter configured to receive an analog signal, e.g., from the probe, amplifier, and/or filter, and to transmit a digital signal; and/or a device (e.g., a computing device, such as a personal computer) configured to receive one or more digital signals as an input and to transmit values for $C_m$ as an output.

The circuit can include any useful probe, such as an electrode that is electrically connected to the pore or fluid in the second chamber. The electrode can be a nanoelectrode, a microelectrode, a wire, or an array of electrodes (e.g., an array of individually addressable electrodes).

The one or more electrical signals can be indicative of transport or lack of transport of the agent through the at least one barrier cell. Non-limiting electrical signals include current, complex admittance, voltage, etc. Such electrical signals can be indicative of other electrical parameters, such as membrane capacitance ($C_m$), membrane conductance ($G_m$), etc. $C_m$, in turn, can include the conductance of the entire cell or the conductance of the membrane patch forming the seal across the pore. Methods of determining $C_m$ are described herein, as well as in Rituper, B., et al., *Nature Protocols*, 2013; 8(6): 1169-1183); Lindau, M. and E. J. P. A. Neher, *Pflügers Archiv European Journal of Physiology*, 1988; 411(2): 137-146; Debus, K. and M. Lindau, *Biophysical Journal*, 2000; 78(6): 2983-2997; and Pusch, M. and E. Neher, *Pflügers Archiv European Journal of Physiology*, 1988; 411(2): 204-211, each of which is incorporated herein by references in its entirety.

Figure 2:
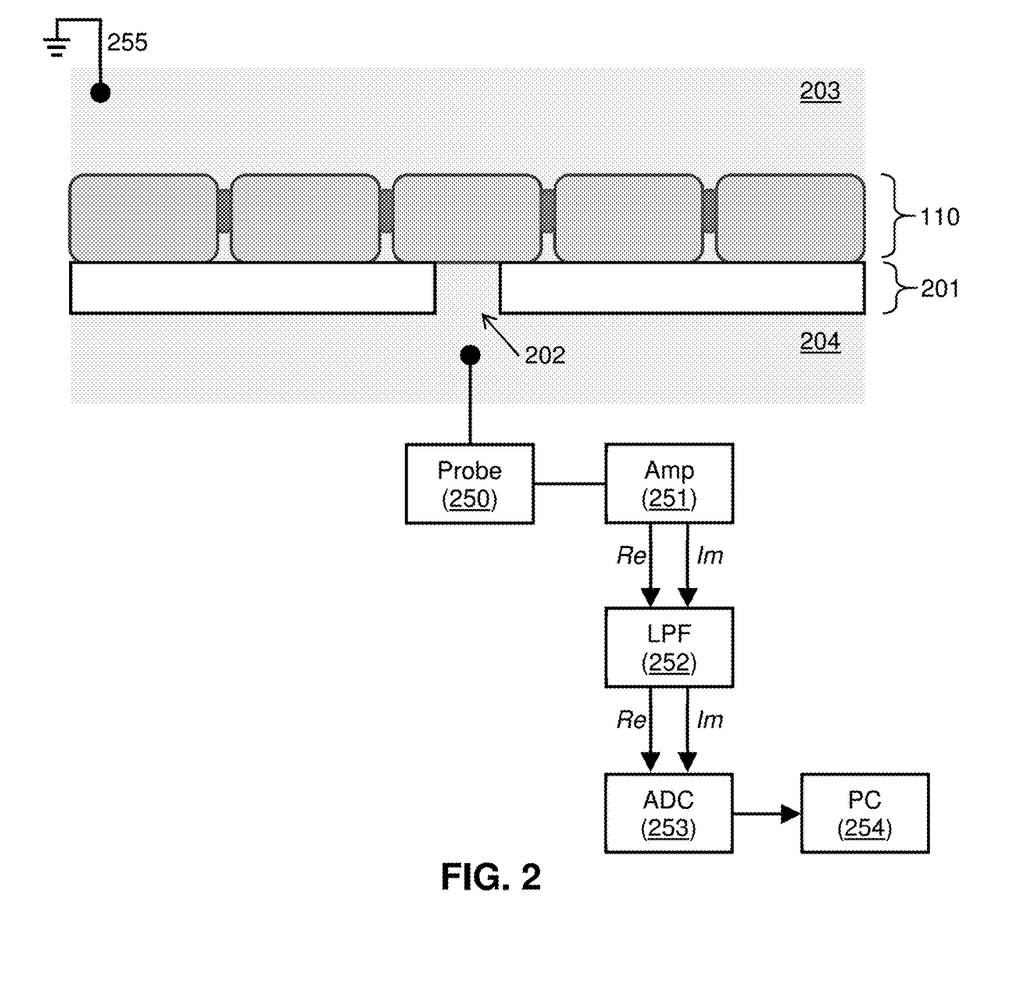
FIG. 2 shows a schematic of a non-limiting system employing an apparatus having a pore 202 and a circuit including a probe 250, an amplifier 251, a low-pass filter 252, an A/D converter 253, and a personal computer 254.

FIG. 2 provides a schematic of a non-limiting system including an apparatus and a circuit. The non-limiting apparatus includes a first chamber 203, a substrate 201 having a pore 202, and a second chamber 204. The first chamber 203 can be configured to culture a layer comprising a plurality of barrier cells 110. As can be seen, the pore 202 is configured to form a seal with at least one barrier cell, and the second chamber 204 in fluidic communication with the at least one pore 202. The non-limiting circuit can include a probe 250 configured to detect an electrical signal within a fluid disposed within the second chamber 204; and a lock-in amplifier (Amp) 251 configured to receive an electrical signal from the probe 250 and to transmit an initial real component (Re) and an initial imaginary component (Im) of complex admittance as output signals. The circuit can further include a low-pass filter (LPF) 252 configured to receive the initial real component and the initial imaginary component and to transmit a filtered real component and a filtered imaginary component; an analog-to-digital converter (ADC) 253 configured to receive the filtered real component and the filtered imaginary component and to transmit a corresponding digital real component signal and a corresponding imaginary component signal; and a device (e.g., a personal computer 254) configured to receive the corresponding digital real component signal and the corresponding imaginary component signal and to transmit a determined $C_m$ (e.g., a determined $C_m$ that is a relative determined $C_m$) as an output.

Figure 3A:
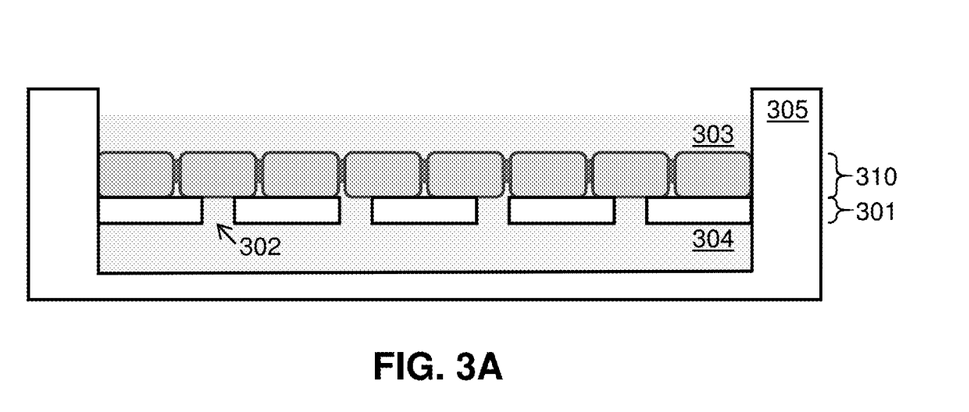
FIGS. 3A-3B show schematics of non-limiting apparatuses that include (A) a substrate 301 having a plurality of pores 302, in which each pore is in fluidic communication with a single second chamber 304; and (B) a substrate 351 having a plurality of pores 352a-352d, in which each pore is in fluidic communication with an individual second chamber (one of 354a-354d).

The apparatus can include a plurality of pores and/or a plurality of wells. As seen in FIG. 3A, a non-limiting apparatus can include a substrate 301 having a plurality of pores 302. The apparatus can include walls 305 that define the first chamber 303 and the second chamber 304. As can be seen, the first chamber 303 is in fluidic communication with each cell within the barrier layer 310, and the second chamber 304 is in fluidic communication with each pore 302 within the substrate.

Figure 3B:
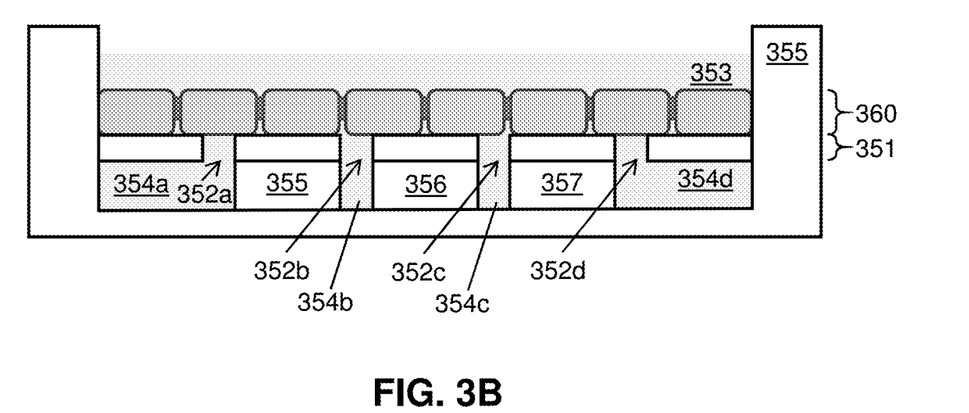

Alternatively, each pore can be individually accessed and characterized. In one instance, the second chamber includes a plurality of wells, and each well is configured to be in fluidic communication with one pore. By using an array of individually addressable electrodes, each electrode can be configured to be in fluidic communication with one well. For example, as seen in FIG. 3B, a non-limiting apparatus can include a substrate 351 having a plurality of pores 352a-352d. The apparatus can include walls 355 that define the first chamber 353 and a portion of wells 354a-354d that form the second chamber. Additional walls 355-357 are used to further define each well 354a-354d, thereby allowing each pore to be accessed by a different well. As can be seen, the first chamber 353 is in fluidic communication with each cell within the barrier layer 360, and each well 354a-354d in the second chamber is in fluidic communication with one pore 352a-352d, respectively, within the substrate.

In another instance, the first chamber and the second chamber are both partitioned into a plurality of wells. When used with a substrate having a plurality of pores, each pore can be individually accessed by a separate well in the first chamber and be individually measured by a separate well in the second chamber. Thus, in some embodiments, a first pore is disposed between a first well in the first chamber and a first well in the second chamber; and a second pore is disposed between a second well in the first chamber and a second well in the second chamber, in which the first and second pores are electrically separated. In other embodiments, each well in the second chamber includes an individually addressable electrode, thereby allowing an electrical measurement only within that well.

The methods, apparatuses, and systems herein can allow for spatial and temporal resolution of electrical signals being generated by the barrier layer. For instance, a method can include measuring one or more electrical signals within each of the plurality of wells by using each of the individually addressable electrodes, thereby providing a plurality of spatially resolved electrical measurements. Each well within an m×n array can provide a particular signal, and the plurality of wells can provide a matrix of m×n measurements for each well in that m×n array. If such m×n measurements are provided over time, the both spatial and temporal resolution across the barrier layer can be obtained.

Also described herein are methods of forming the substrate having one or more pores. The substrate can be formed by pre-treating the top surface of the substrate with a chemical agent (e.g., a silane), a biological agent (e.g., a protein, such as poly-L-lysine or other proteins herein), or a plasma (e.g., $O_2$ plasma).

Figure 4:
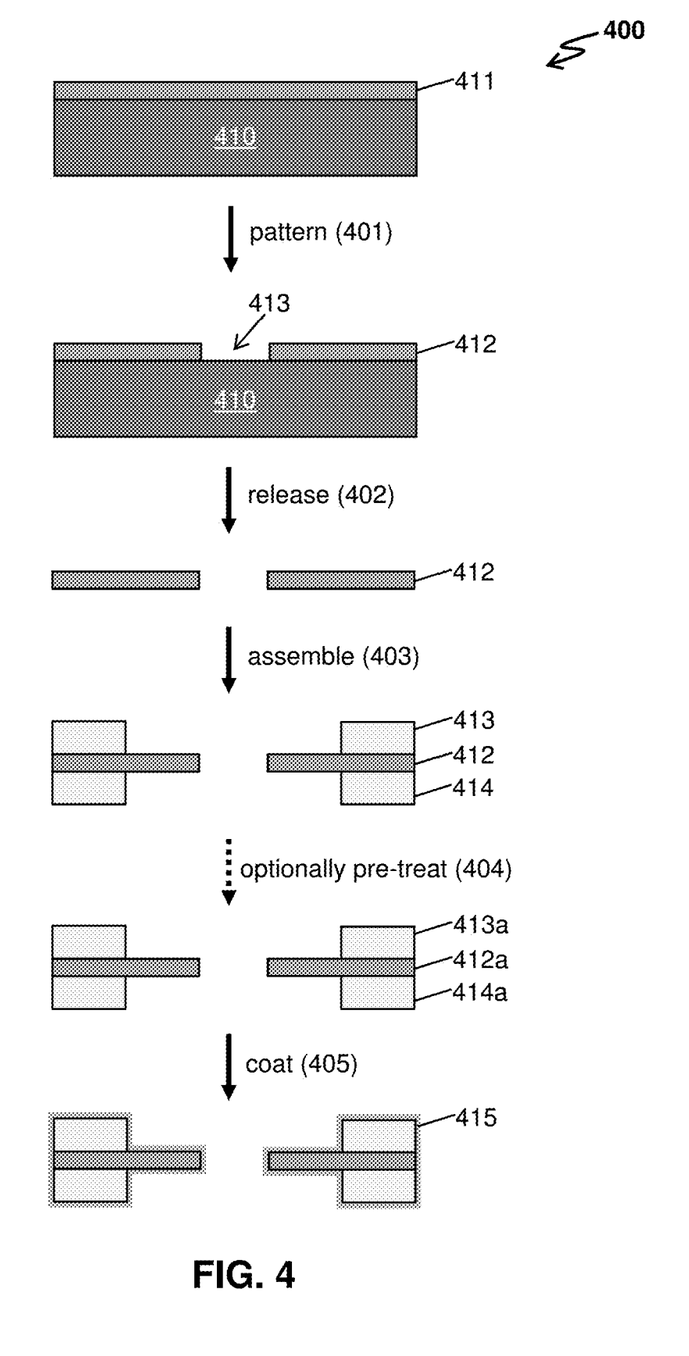
FIG. 4 shows a non-limiting schematic of a process 400 to form an apparatus.

FIG. 4 provides a non-limiting process 400 for forming the substrate, which includes operation 401 of patterning a substrate layer 411 disposed on a carrier 410 to form a pore 413 within the substrate 412; and operation 402 of releasing the patterned substrate 412. In some embodiments, the released substrate is a planar substrate. The substrate layer can be a photoresist layer, in which patterning can then be photopatterning the photoresist layer to form a pore. In other embodiments, the substrate layer can include another material (e.g., glass, silica, etc.), in which patterning can include ablating or drilling the substrate to form the pore.

The process can include operation 403 of assembling the substrate 412 with a first assembly 413 to form the first chamber and a second assembly 414 to form the second chamber. The first and second assembly 413,414 can include a ring (e.g., an O-ring), a molded layer, a chamber layer, or other layer having an opening to form the chambers when assembled.

The process can optionally include an operation 404 for pre-treating the surface of the substrate, pore, first chamber, and/or second chamber with an agent (e.g., a chemical agent, a biological agent, or a plasma) to sterilize, activate, or otherwise modify the surface. Finally, the process can include an operation 405 for coating an exposed surface (e.g., of the substrate, pore, first chamber, and/or second chamber) with a protein, polymer, or other agent. Such a coating can provide a biocompatible surface or an amenable surface for growth and/or culture of the barrier layer.

EXAMPLES

Example 1: Real-Time Patch-Clamp Sensing of Transport Across a Blood-Brain Barrier Models of the Blood-Brain Barrier (BBB) can enable the development of medical countermeasures capable of accessing the brain. Current efforts towards advancing brain-related drug development are hindered by a lack of high-resolution detection strategies for measurement of active transport.

The BBB is a semipermeable interface that separates circulating blood from the central nervous system. It includes tight junctions between endothelial cells of blood vessels that form a critical line of defense against threats to the brain (see, e.g., Daneman, R. and A. Prat, "The blood-brain barrier," *Cold Spring Harbor Perspectives in Biology*, 2015; 7(1): a020412 (23 pp.)). Evaluations with BBB models can provide insights during the development of effective therapies that are capable of penetrating into the brain. While progress has been made towards establishing physiological representation with a variety of in vivo and in vitro strategies, there is no current method capable of accurately quantifying the ability of chemical and biological agents to cross the BBB in real-time.

Existing approaches are limited because they (i) don't provide spatiotemporal information, (ii) rely on terminal end points for experiments, and (iii) have limited potential for quantification. Most existing BBB studies have limited potential for acquiring mechanistic understanding because they rely heavily on animal models, with each animal representing only a single experimental time point (see, e.g., O'Brown, N. M., S. J. Pfau, and C. Gu, "Bridging barriers: a comparative look at the blood-brain barrier across organisms," *Genes & Development*, 2018; 32(7-8): 466-478).

Described herein are methods, apparatuses, and systems to incorporate electrical patch-clamp monitoring to allow quantification of transport across brain endothelial cells in real-time. Patch-clamp is a highly sensitive micropipette recording technique that is commonly used in electrophysiology to record activity of individual ion channels on cell membranes (see, e.g., Neher, E. and B. J. S. A. Sakmann, "The patch clamp technique," *Scientific American*, 1992; 266(3): 44-51). It involves forming a tight gigaohm seal against the surface of a membrane and amplifying the electrical response across the membrane patch in response to an applied voltage or current clamp. The method has also been used to quantify vesicle fusion to membranes through measurement of capacitance, with a resolution sufficient for detecting individual vesicles (see, e.g., Lindau, M. and E. J. P. A. Neher, "Patch-clamp techniques for time-resolved capacitance measurements in single cells," *Pflügers Archiv European Journal of Physiology*, 1988; 411(2): 137-146; and Debus, K. and M. Lindau, "Resolution of patch capacitance recordings and of fusion pore conductances in small vesicles," *Biophysical Journal*, 2000; 78(6): 2983-2997). While capacitance-based detection of exocytosis and endocytosis has been demonstrated for various cells, patch-clamp has not been previously applied to investigate transport across adherent endothelial barrier tissues (see, e.g., Rituper, B., et al., "High-resolution membrane capacitance measurements for the study of exocytosis and endocytosis," *Nature Protocols*, 2013; 8(6): 1169-1183).

Without wishing to be limited by mechanism, active transport by the BBB generally involves the formation of lipid vesicles to encapsulate the agent at the luminal surface of endothelial cells and travel across the cell and to the basal membrane. Such lipid vesicles would then fuse to the basal membrane, thus releasing the agent out of the endothelia cell and into the neural side of the brain. As the vesicle fuses with the basal membrane, the surface area of the membrane increases, and this increase can be electrically detected by a patch-clamp type apparatus. For instance, membrane capacitance ($C_m$) is generally proportional to cell surface area, and fluctuations in cell surface area (e.g., during vesicle fusion) can be monitored by observing changes in $C_m$. In particular embodiments, monitoring of $C_m$ could allow for label-free detection of agent transport.

However, conventional methods for patch-clamp recording are not well-suited for studying the activity of a living barrier tissue because endothelial cells must adhere tightly to a surface, forming a thin layer that is difficult to patch with a micropipette. Furthermore, as endothelial cells must also remain functionally viable and unimpeded by the recording process, patches of endothelial membrane are insufficient. Rather, the whole endothelial cell must remain intact during detection.

Described herein are methods, apparatuses, and systems that include growing cells over recording micropores that allow endothelial cells to form gigaohm seals. A batch microfabrication process was established for high-throughput manufacture of cell culture compatible surfaces with recording micropores. Endothelial layers cultured over the micropores could form tight gigaohm seals without damaging cell viability or disrupting barrier function. By confirming the presence of gigaohm seals, such electrical monitoring approaches can be adapted by using arrays of micropores that would enhance spatiotemporal resolution. Additional details follow.

Example 2: Experimental Methods

Microfabrication: A photolithography mask was designed using CAD software to display patterns for 7 mm discs with micropore structures and transferred to chrome on 5"×5" soda lime glass (Photo Sciences, Inc.). Then, 4" test grade silicon wafers were dehydrated at 150° C. on a hot plate for 10 minutes and then treated with fluorinated trichlorosilane (United Chemical Technologies (UCT)) in a vacuum chamber. A 20 µm layer of SU8 2025 photoresist (MicroChem Inc.) was applied to the wafer, exposed to produce micropore patterns using a Karl-Suss MA6 contact aligner with a long-pass UV filter (Omega Optical, LLC), and then developed in SU8 Developer (MicroChem) according to manufacturer protocols. Discs with micropore structures were rinsed with isopropanol and deionized water, and then released from the wafer. Discs were soaked in ethanol for sterilization, and then placed between two sealing rings punched out of a 1 mm thick layer of polydimethylsiloxane (PDMS) (Sylgard 184, Ellsworth Adhesive Co.). Devices were further sealed with an additional 500 nm layer of Parylene-C deposited conformally using a SCS Labcoter PDS-2010 instrument according to manufacturer protocols. Sealed discs were rinsed with Dulbecco's Phosphate Buffered Saline (DPBS, Thermo Fisher Scientific Inc.) and kept sterile until used for cell culture.

Cell Culture: bEnd.3 mouse brain endothelial cells (ATCC) were cultured in high-glucose Dulbecco's Modified Eagle Medium (DMEM) supplemented with 10% fetal bovine serum (Gibco), 100 U/mL penicillin, and 100 µg/mL streptomycin (Invitrogen) in a humidified incubator at 5% CO2 and 37° C. ambient temperature. Cells were lifted with 0.25% trypsin with tetrasodium ethylenediaminetetraacetic acid (EDTA, Gibco) for routine passaging and were seeded for culture at a density of 20,000 cells/cm2.

Immunofluorescence: Adherent cells were fixed with 4% paraformaldehyde (Electron Microscopy Sciences, Inc.) for 20 minutes and then washed with DPBS. Cells were permeabilized in an ice-cold solution of 1:1 of methanol: acetone for 1 minute, washed once with DPBS, then treated with blocking buffer (5% fetal bovine serum in DPBS) for 1 hour at room temperature. Samples were then incubated with the primary antibodies, which included: 10 µg/mL rabbit monoclonal anti-transferrin receptor (Abcam, clone EPR20584, isotype IgG) or 1:100 diluted rabbit polyclonal anti-transferrin receptor (Thermo Fisher, PAS-27739, isotype IgG), 10 µg/mL rat anti ZO-1 (Thermo Fisher, clone R26.4C, isotype IgG2a), and 5 µg/mL rat monoclonal anti-VE cadherin (Abcam, clone BV13, isotype IgG1) diluted in blocking buffer. Primary antibodies were subsequently removed, and samples were washed with DPBS three times for 5 minutes each. The secondary antibodies were then applied, including: goat anti-rabbit IgG (H+L) conjugated to Alexa Fluor 647 (Thermo Fisher), mouse anti-rat IgG2a conjugated to FITC (BioLegend, clone MRG2a-83), and mouse anti-rat IgG1 conjugated to Phycoerythrin (BioLegend, clone MRG1-58). Secondary antibodies were subsequently removed, and samples were washed with DPBS three times for 5 minutes each. All antibody incubation steps were carried out for 6-8 hours at 4° C. Then, 1 µg/mL of 4',6-diamidino-2-phenylindole (DAPI) (Invitrogen) was then added as a nucleic acid stain. Finally, samples were mounted on glass cover slips with Prolong Diamond antifade mountant (Thermo Fisher) and imaged using an EVOS FL Digital Color Fluorescence Microscope.

Patch-Clamp Recording: The phase-tracking system for patch-clamp recording was set up as previously described (see, e.g., Rituper, B., et al., *Nature Protocols*, 2013; 8(6): 1169-1183) using the following components: Axon CNS Molecular Devices Axopatch 200B, CV 203BU Headstage, Axon CNS Molecular Devices Digidata 1440A Low Noise Data Acquisition System, Stanford Research Systems Model SR830 DSP Lock-in Amplifier, Agilent Technologies, InfiniiVision DSO-X 4024A oscilloscope. The sample chamber was heated using a 5 W, 33Ω power resistor supplied by an Agilent E3620A DC Power Supply. The patch-clamp headstage was supported by an aluminum optical table clamp and shielded by a grounded stainless-steel mesh. Temperature was monitored using a Fluke 87 III True RMS Multimeter with an 80TK Thermocouple module. The micropore sample chamber was used with an Ag/AgCl electrode and inlet tube at a thermocouple reading of 38 mV (equivalent to 38° C.). Recording instrumentation included the patch-clamp amplifier, a digitizer, and a lock-in amplifier. An oscilloscope was employed to show the stimulatory signal from the lock-in amplifier and the output of the patch-clamp amplifier.

Example 3: Fabrication and Characterization of Micropore Test Structures

Figure 5A:
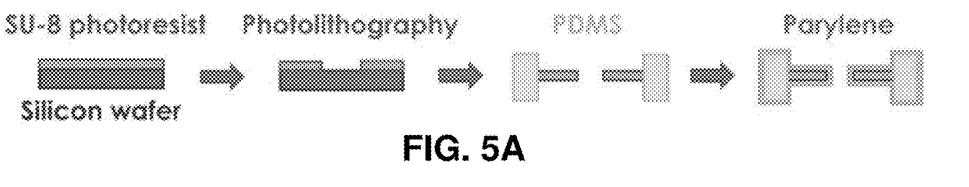
FIGS. 5A-5C show fabrication and characterization of non-limiting micropores. Provided are (A) a schematic showing microfabrication workflow for SU8 discs with micropores including sealing with parylene-C; (B) an image of a 4" silicon wafer with developed SU8 discs after thermal reflow and prior to release, in which insets show microscope views of the top and bottom of an individual micropore with indicated diameters and a 17×17 micropore array; and (C) an image of a commercially available borosilicate glass micropore on a Nanion chip, in which the inset shows a closeup of the 2 µm diameter micropore.

SU8 discs were successfully fabricated and released from silicon wafers with a process yield of >80% under optimized photolithography conditions. While the ultimate target diameter for micropores was 1-3 µm for optimal patch-clamp (see, e.g., Okada, Y., "Patch Clamp Techniques: From Beginning to Advanced Protocols," 2012, Springer (Tokyo, Japan), 439 pp.), the photolithography mask was designed with 7 µm pores to account for process variation and to allow subsequent tuning of the pore size upon sealing with parylene-C polymer (FIG. 5A).

Figure 5B:
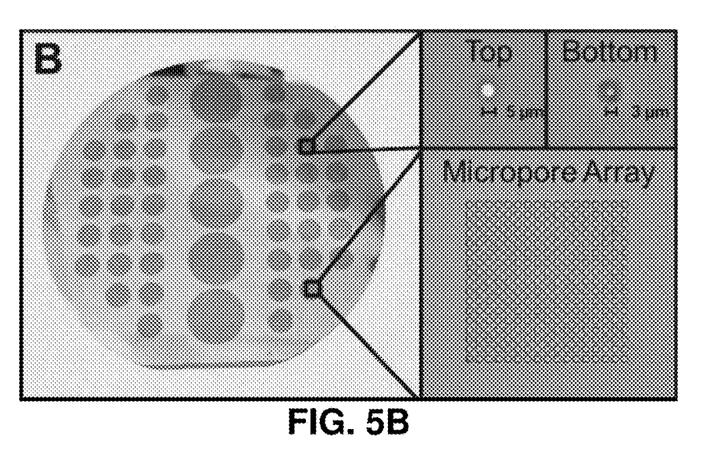
Figure 5C:
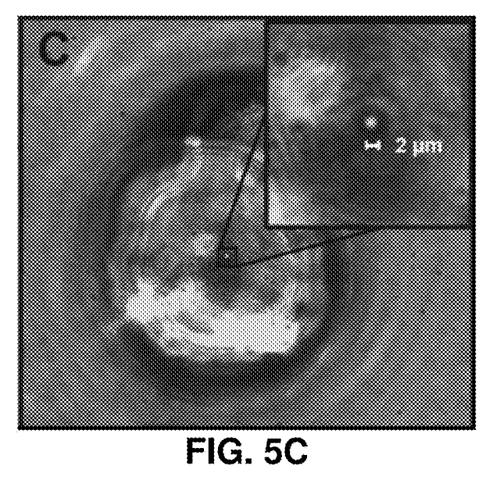

After release of the SU8 discs, the top and bottom diameters of the micropores were measured to be 5 µm and 3 µm, respectively, as determined by optical microscopy and analysis with the software ImageJ (NIH). With a disc thickness of 20 µm, this corresponds to a sidewall profile with an angle of about 84°. Defects and cracks present in the SU8 layer were corrected by thermal reflow at 150° C. for 10 minutes, and then discs were gradually cooled to room temperature to relieve thermal stresses. This resulted in a smooth surface with well-defined geometries for both single pores and arrays (FIG. 5B). SU8 micropores had a clear profile and did not display optical distortion around micropores, as typically seen with commercially available patch-clamp chips fabricated from borosilicate glass (FIG. 5C).

Example 4: Endothelial Cell Culture Over Micropores

Figure 6A:
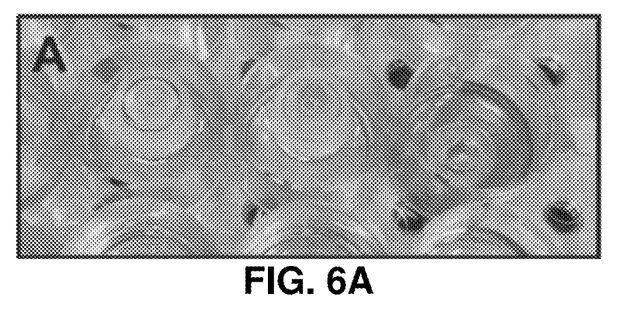
FIGS. 6A-6G show a non-limiting culture of bEnd.3 cells over micropore structures. Provided are (A) images of PDMS gaskets used to form wells for cell culture on a Nanion Patch Clamp chips (left well is empty, middle has seeded cells) and on a 7 mm SU8 disc (right) in humidified culture chambers; and microscope images of confluent cell layers after 48 hours of culture on (B) a Nanion Patch Clamp chip, in which the inset shows a closeup of area around the 2 µm diameter pore, (C) a parylene-C coated SU8 disc with a 2 µm diameter pore, and (D) a micropore array. Immunofluorescence images of confluent cell layers confirm expression of (E) zona occludens-1 (ZO-1) tight junction protein, (F) vascular endothelial (VE)-cadherin barrier marker, and (G) transferrin receptor. DAPI nucleic acid stain is shown in dark gray in FIGS. 6E-6F. All scale bars are 20 µm.
Figure 6B:
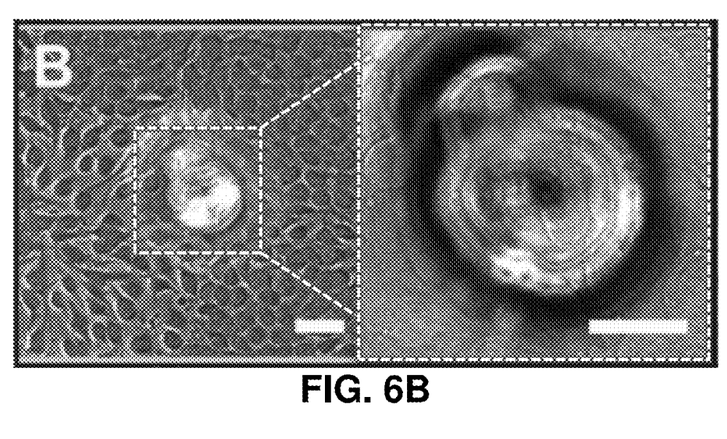
Figure 6C:
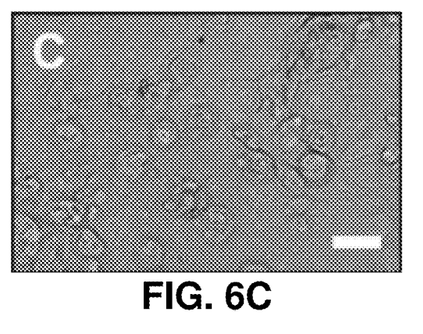
Figure 6D:
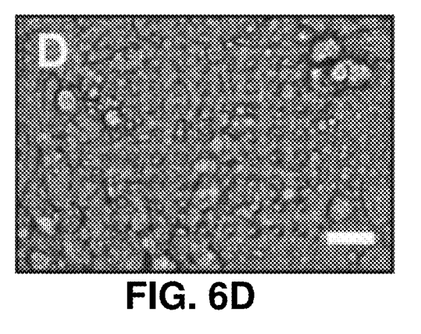

Micropore surfaces were sterilized with ethanol, sealed with PDMS gaskets (except for parylene-C coated discs, which had already been sealed), then treated with 100 μg/ml poly-L-lysine (Sigma-Aldrich) to facilitate cell adhesion (FIG. 6A). The bEnd.3 cells were observed to attach within 12 hours of seeding, and confluent layers were fully formed within 48 hours (FIGS. 6B-6D). Confluent cell layers remained intact for at least three days with >99% viability, as determined by dye exclusion after staining with 0.4% Trypan Blue solution (Logos Biosystems).

Figure 6E:
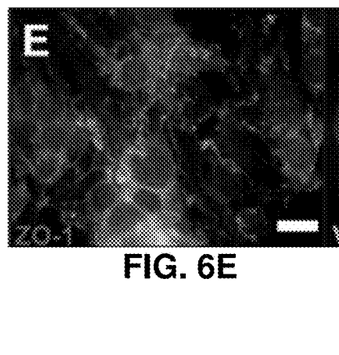
Figure 6F:
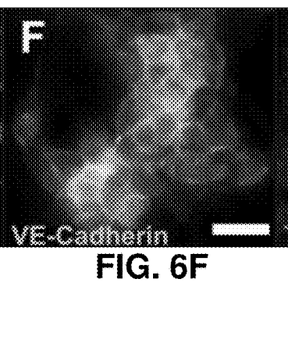
Figure 6G:
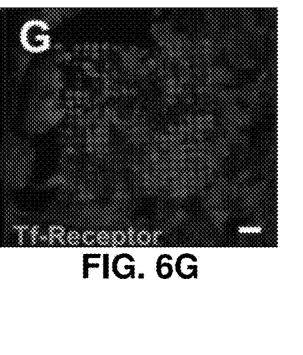

Cell layers restricted passage of 70 kDa Dextran-Texas Red (Thermo Fisher) when treated at a concentration of 75 nM for up to 6 hours. The presence of tight junctions between cells was confirmed through immunofluorescent staining using antibodies for the markers ZO-1 and VE-cadherin (FIGS. 6E-6F). Confluent layers also expressed transferrin receptor, though specific polarization or localization on the membrane surface was not apparent after three days of culture (FIG. 6G).

Example 5: Electrical Detection Across Micropores

Figure 7:
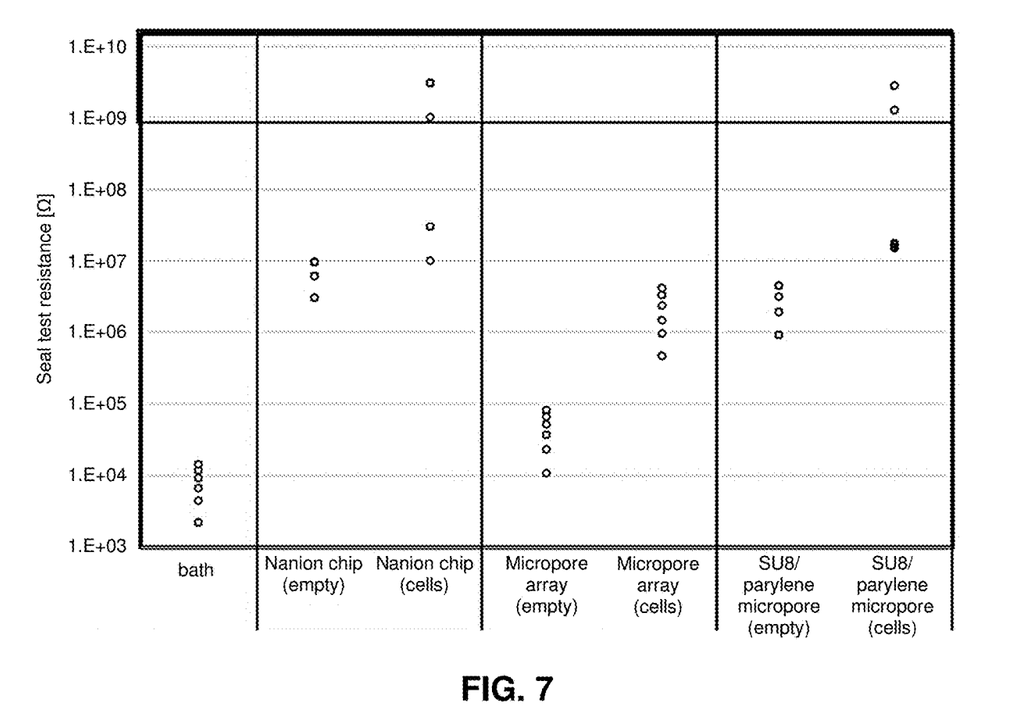

Seal tests were performed to evaluate the electrical integrity of seals formed across micropores by the cultured endothelial cells. Micropores were loaded into a sample chamber and connected to Ag/AgCl electrodes through droplets of 0.1 M PBS. The Axopatch 200B instrument was used to apply an oscillating 5 mV voltage step at a 40-60% duty cycle. The measured resistance values across the micropores are plotted in FIG. 7. Gigaohm seals (e.g., seals of $10^9 \Omega$ or greater) were successfully achieved for 50% of Nanion chips (2/4), 0% of SU8 micropore arrays (0/6), and 33% of parylene-coated SU8 micropores (2/6). Some of the seals for the micropore arrays provided a partial seal (e.g., a megaohm seal) having a resistance of $10^6 \Omega$ or greater.

Figure 8:
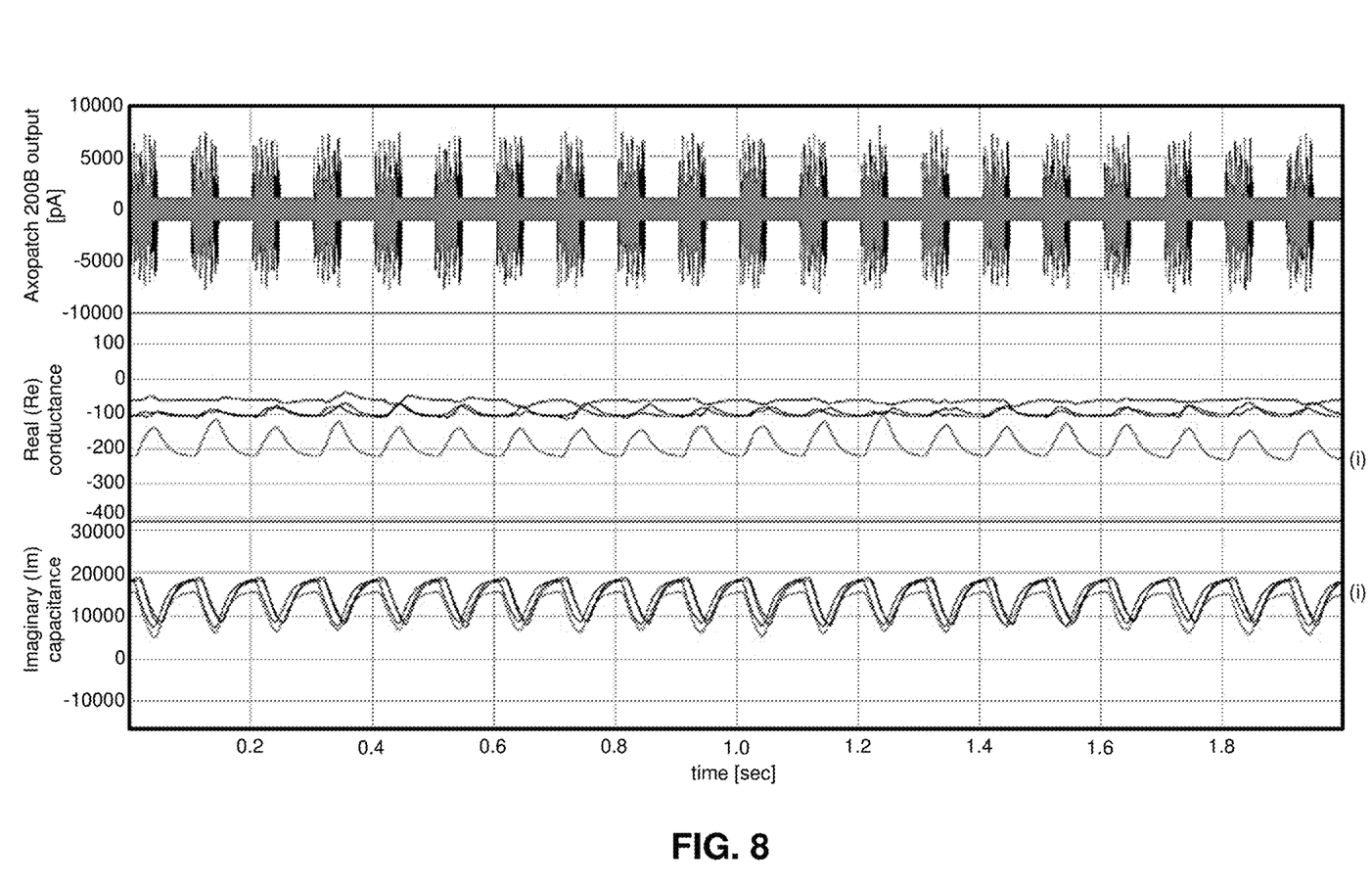
FIG. 8 shows phase angle calibration for a parylene-coated SU8 micropore with gigaohm patched cell layer. Four sweeps (lasting two seconds each) are overlaid, in which the initial sweep is gray in the top graph and labeled with (i) in the lower two graphs. The output for Axopatch 200B shows calibration pulses applied at 10 Hz. The response from the calibration pulses was eliminated gradually from the Real signal (middle graph) by increasing the phase angle+54 degrees.

Patched BBB models with successful gigaohm seals (n=4) were then stimulated with a 0.11 mV sine wave signal at 1.6 Hz frequency for cell-attached recording, as previously described (see, e.g., Rituper, B., et al., *Nature Protocols*, 2013; 8(6): 1169-1183). Measurement of changes in capacitance required a phase angle calibration to resolve complex admittance with separated components for conductance and capacitance. A DR-1 series dither unit (Molecular Devices, LLC) was connected between the Ag/AgCl bath electrode and ground to transiently apply a 500 kΩ resistor in series at a frequency of 10 Hz. The phase angle on the lock-in amplifier was adjusted until the 10 Hz dithering calibration pulses appeared only on the Capacitance (Imaginary component) and not Conductance (Real component) output (FIG. 8).

Micropores have been previously developed for patch-clamp applications to facilitate high-throughput measurements and automated recording from cells (see, e.g., Okada, Y., "Patch Clamp Techniques: From Beginning to Advanced Protocols," 2012, Springer (Tokyo, Japan), 439 pp; and Fertig, N., et al., "Stable integration of isolated cell membrane patches in a nanomachined aperture," *Applied Physics Letters*, 2000; 77(8): 1218-1220). Here, micropore structures were manufactured directly from the photosensitive epoxy SU8 by photolithography. This technique allows for rapid and inexpensive fabrication of well-defined pore geometries. Compared with conventional patch-clamp micropore fabrication techniques that employ etching or laser-based milling (see, e.g., Fertig N., et al., "Microstructured glass chip for ion-channel electrophysiology," *Physical Review E*, 2001; 64(4): 040901 (4 pp.); Pantoja, R., et al., "Silicon chip-based patch-clamp electrodes integrated with PDMS microfluidics," *Biosensors and Bioelectronics*, 2004; 20(3): 509-517; and Bruhn, B. R., et al., "Dual-pore glass chips for cell-attached single-channel recordings," *Lab on a Chip*, 2014; 14(14): 2410-2417), this one-step lithography technique enables higher throughput batch production, and allows direct integration with microfluidic channels and electrodes. In addition, arrays having multiple micropores were easily fabricated with no additional effort. SU8 structures were sealed within a PDMS assembly by conformal deposition of parylene-C, which permitted further reduction of pore diameters. Of note, parylene is a United States Pharmacopeia (USP) Class VI biocompatible polymer that is compatible with both electrophysiology and cell culture (see, e.g., Zhang, L., et al., "Enhanced parylene-C fluorescence as a visual marker for neuronal electrophysiology applications," *Lab on a Chip*, 2018; 18(23): 3539-3549; and Chang, T. Y., et al., "Cell and protein compatibility of parylene-C surfaces," *Langmuir*, 2007; 23(23): 11718-11725).

Brain endothelial cells were cultured to form a model BBB over microfabricated discs and commercially available borosilicate glass micropore chips. SU8, parylene, and glass surfaces treated with poly-L-lysine allowed successful formation of barriers within three days. Immunofluorescence assays confirmed the expression of properly localized ZO-1 and VE-cadherin proteins at the interfaces between adjacent cells, which indicates the presence of tight junctions. Tissue layers remained viable as determined by effective exclusion of the membrane impermeable dye Trypan Blue, and demonstrated appropriate barrier function by preventing the passive diffusion of fluorescently labeled 70 kDa dextran. The bEnd.3 cells also expressed transferrin receptor, which is involved with active transport of transferrin protein. During the active transport process, extracellular transferrin interacts with the receptor at the luminal membrane, enters the cell body through a vesicle, and is then transported to the basolateral surface of the cell (see, e.g., Wiley, D. T., et al., "Transcytosis and brain uptake of transferrin-containing nanoparticles by tuning avidity to transferrin receptor," *Proceedings of the National Academy of Sciences of the United States of America*, 2013; 110(21): 8662-8667). However, transferrin receptor proteins did not appear to localize on the cell membrane surface after three days of culture, and it is expected that a longer culture time would be required for the tissue layer to fully develop active transport capabilities. Further studies with micropores herein could be extended to provide longer culture times.

Successful application of the patch-clamp technique is dependent on the formation of a highly resistive electrical seal against the recording micropore. If this gigaohm level seal is not properly maintained, the leakage of current could result in excessive levels of noise that obscure any useful measurement. Electrical seal tests using oscillating voltage steps demonstrated that the bEnd.3 cells were capable of spontaneously forming gigaohm seals over parylene coated micropores and Nanion micropore chips. The observed efficiency for seal formation did not exceed 50%, and would likely be improved by further optimization of micropore geometry, material, and surface treatment. Other strategies such as introducing osmolarity gradients could be beneficial. The presence of a gigaohm seal did not appear to cause adverse effects on cell viability or barrier function.

The measurement of changes in cell membrane capacitance requires that the quantity of interest within the patched membrane can be resolved from stray capacitances by the value of its time constant. Resolution of these measurements on whole cells would be limited by the magnitude of Johnson thermal agitation noise of the access resistance (see, e.g., Debus, K. and M. Lindau, *Biophysical Journal*, 2000; 78(6): 2983-2997). With the cell-attached mode of patch-clamp, a seal is formed on a particular location of a cell without rupturing the membrane, and thus capacitance is measured across two lipid bilayers: the patch itself and the remaining cell membrane. While the added variables of a second membrane layer do not allow measurement of absolute values for capacitance, this method enables relative measurements of the ratio of capacitances between the patch and outer cell membrane with an extremely high signal to noise ratio. Since measurements are relative and not absolute, they cancel out the majority of noise and allow the detection of capacitance changes that are 1000 times smaller than the resting capacitance (see, e.g., Rituper, B., et al., *Nature Protocols*, 2013; 8(6): 1169-1183). By appropriately setting the amplitude and frequency of the stimulatory sine wave signal, this approach can achieve 15 aF resolution, which is capable of detecting the fusion of even a single small vesicle (see, e.g., Debus, K. and M. Lindau, *Biophysical Journal*, 2000; 78(6): 2983-2997).

Since the cultured bEnd.3 cells were not capable of active transport within the three day cell culture timeframe used in this study, changes in capacitance were modeled using a series resistance dithering circuit. The circuit was used to apply calibration pulses through a gigaohm sealed bEnd.3 layer over a parylene-coated micropore at a frequency of 10 Hz. The readout from the lock-in amplifier was used to determine an appropriate phase angle for the stimulatory sine wave signal that successfully isolated the conductance component from changes in capacitance. Additional experiments can include longer culture timeframes, which can enhance formation of gigaohm seals between each cell within the layer.

Example 6: Further Uses and Assemblies

Figure 9A:
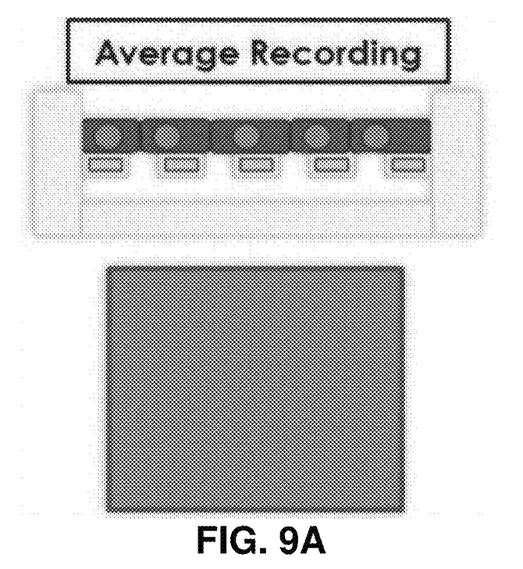
FIGS. 9A-9B show non-limiting pore arrays. Provided are schematics of (A) an array configured to provide an average recording of all cells (top), in which the spatial signal from each pore within the array provides the same, average response (bottom); and (B) an array configured to provide discrete recordings within a well or chamber (top), in which the spatial signal from each pore within the array could provide a discrete response for each cell associated with that pore (bottom).
Figure 9B:
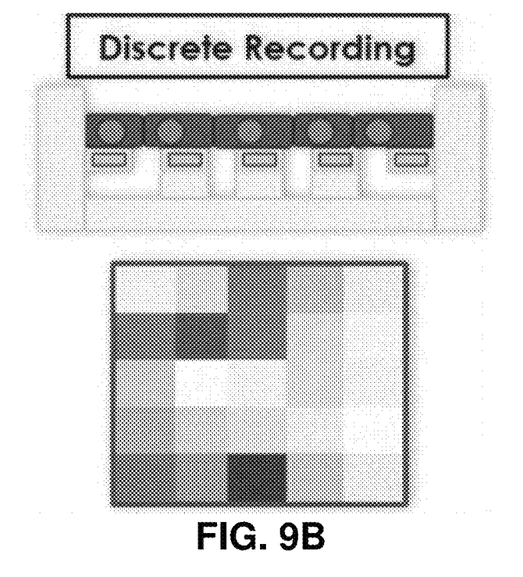

Micropore arrays could be used to establish high levels of spatiotemporal resolution for patch-clamp and allow the testing of a wide variety of experimental conditions on a single cultured barrier tissue layer (FIGS. 9A-9B). The use of SU8 batch microfabrication also simplifies the manufacture of other structures such as microwells, filters, and scaffolds; and assemblies herein can include such structures.

As described herein, we evaluated the feasibility for incorporating patch-clamp for real-time quantification of active transport across a barrier tissue. Based on our knowledge, there was a lack of prior evidence showing that cultured endothelial cells can form gigaohm seals without disturbing barrier function or cell viability. Here, we demonstrated that bEnd.3 cells can form viable tissue barriers with gigaohm seals patched over 2 µm diameter micropores.

Further adaptations can include improving the efficiency of seal formation. For instance, the modification of the physical and chemical properties of silicon micropores has been shown to improve sealing efficiency for cell contact induced by vacuum (see, e.g., Sordel, T., et al., "The development of high quality seals for silicon patch-clamp chips," *Biomaterials*, 2010; 31(28): 7398-7410). Other strategies for improving seal formation can include optimizing the geometry of the pore, the material of the pore, surface characteristics and treatments to the surface (e.g., charge, roughness, chemical moieties, etc.), and optimizing culture conditions including temperature, pH, and the composition of the culture medium. It is expected that there are additional strategies that can be developed to exploit the natural mechanisms of cell spreading and adhesion that occur during cell culture.

Other modifications can include those to more closely mimic the BBB. Thus, in one embodiment, the methods, apparatuses, and systems herein can include use of a representative blood component on the corresponding luminal surface of the cell culture. Blood is an extremely complicated biological fluid that can interfere with many assays and complicates detection by optical methods. Pursuing label-free electrical sensing, as described herein, could be one approach to simplify detection in systems that employ blood.

The methods, apparatuses, and systems herein can provide tools for brain-related drug discovery, and platforms for screening the ability of chemical, or biological agents to access the brain and the central nervous system. Yet other studies can include determining the molecular mechanisms of BBB disruption in traumatic brain injury (TBI). When the brain is subjected to mechanical trauma, the integrity of the BBB is disrupted, which can affect cerebral blood flow and cause neuronal degeneration (see, e.g., Chodobski, A., B. J. Zink, and Szmydynger-Chodobska J., "Blood-brain barrier pathophysiology in traumatic brain injury," Translational Stroke Research, 2011; 2(4): 492-516). The mechanism and extent of this disruption is poorly understood, and would benefit from in vitro models that enable real-time sensing.

Current efforts in industrial and research settings rely heavily on animal models, lack spatiotemporal resolution, and have limited potential for acquiring mechanistic understanding. Real-time quantification methods could improve the physiologic relevance of in vitro models for eventual replacement of animal studies. Furthermore, improved in vitro systems can justify the development of models using human cells. This could overcome known limitations with rodent models that do not accurately represent response in humans due to variations with expression of specific membrane protein pumps (e.g., P-glycoprotein (P-gp) and breast cancer resistance protein (BCRP)) (see, e.g., Ball, K., et al., "Physiologically based pharmacokinetic modelling of drug penetration across the blood-brain barrier-towards a mechanistic IV/VE-based approach," *The AAPS Journal*, 2013; 15(4): 913-932).

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A system comprising:
   a first chamber;
   a cultured layer disposed within the first chamber, wherein the cultured layer comprises a plurality of barrier cells seeded and then maintained within the first chamber, and wherein the cultured layer comprises tight junctions and/or adherens junctions;
   a substrate comprising one or more pores disposed within the substrate, wherein at least one pore is configured to form a seal with at least one barrier cell, and wherein at least one pore is a micropore or a nanopore;
   a second chamber in fluidic communication with the at least one pore;
   a probe configured to detect an electrical signal within a fluid disposed within the second chamber; and
   a circuit configured to receive the electrical signal as an input signal and to transmit a real component and an imaginary component of complex admittance as output signals.

2. The system of claim 1, wherein a surface of the substrate and/or the at least one pore comprises a conformal layer of a polymer.

3. The system of claim 1, wherein the substrate comprises a plurality of pores, the second chamber comprises a plurality of wells, and each well is configured to be in fluidic communication with one pore.

4. The system of claim 3, further comprising a probe or an array of individually addressable probes, wherein at least one probe is configured to be in fluidic communication with one well and wherein the at least one probe is configured to detect an electrical signal within a fluid disposed within the one well.

5. The system of claim 1, wherein the seal is characterized as a gigaohm seal.

6. The system of claim 1, wherein the circuit comprises:
   a lock-in amplifier configured to receive an electrical signal from the probe and to transmit an initial real component and an initial imaginary component of complex admittance as output signals; and
   a device configured to receive the output signals and to transmit a determined membrane capacitance as an output.

7. The system of claim 1, further comprising:
   a device configured to receive the current measurement and to transmit a determined membrane capacitance as an output.

* * * * *